US012734256B2

(12) United States Patent
Bar et al.

(10) Patent No.: US 12,734,256 B2
(45) Date of Patent: Sep. 15, 2026

(54) MRI CONTRAST AGENT FOR USE IN THE DIAGNOSIS OF EARLY CHANGES IN THE ENDOTHELIUM OF BLOOD VESSELS

(71) Applicants: UNIWERSYTET JAGIELLONSKI, Cracow (PL); LIPID SYSTEMS SP. Z O.O., Wroclaw (PL)

(72) Inventors: Anna Bar, Przemysl (PL); Tomasz Borowik, Cracow (PL); Stefan Chlopicki, Cracow (PL); Marek Langner, Wroclaw (PL); Magdalena Przybylo, Wroclaw (PL)

(73) Assignees: UNIWERSYTET JAGIELLONSKI, Cracow (PL); LIPID SYSTEMS SP. Z O.O., Wroclaw (PL)

(*) Notice: Subject to any disclaimer, the term of this patent is extended or adjusted under 35 U.S.C. 154(b) by 904 days.

(21) Appl. No.: 17/433,657

(22) PCT Filed: Mar. 11, 2020

(86) PCT No.: PCT/PL2020/050021
§ 371 (c)(1),
(2) Date: Aug. 25, 2021

(87) PCT Pub. No.: WO2020/185104
PCT Pub. Date: Sep. 17, 2020

(65) Prior Publication Data

US 2022/0143224 A1 May 12, 2022

(30) Foreign Application Priority Data

Mar. 11, 2019 (PL) ........................................ 429231

(51) Int. Cl.

| | |
|---|---|
| ***A61K 49/08*** | (2006.01) |
| ***A61K 49/18*** | (2006.01) |
| *B82Y 5/00* | (2011.01) |
| *B82Y 30/00* | (2011.01) |
| *B82Y 40/00* | (2011.01) |

(52) U.S. Cl.
CPC ........ *A61K 49/1812* (2013.01); *A61K 49/085* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | | | |
|---|---|---|---|---|
| 2005/0112065 A1* | 5/2005 | Drummond ............ | A61K 47/36<br>424/9.34 |
| 2009/0155181 A1* | 6/2009 | Rowe .................. | A61K 49/189<br>424/9.3 |

FOREIGN PATENT DOCUMENTS

| | | |
|---|---|---|
| WO | 2005/016141 A1 | 2/2005 |

OTHER PUBLICATIONS

Wikipedia (https://en.wikipedia.org/wiki/Distearoylphosphatidylcholine (downloaded Nov. 13, 2025)). (Year: 2025).*
Phinikaridou, Alkystis, et al., "Increased Vascular Permeability measured With an Albumin-Binding Magnetic Resonance Contrast Agent Is a Surrogate Marker of Rupture-Prone Atherosclerotic Plaque," Circ Cardiovasc Imaging, 2016;9:e004910.
International Search Report, PCT/PL2020/050021, mailed Jul. 17, 2020.
Written Opinion of the International Searching Authority, PCT/PL2020/050021, mailed Jul. 17, 2020.

* cited by examiner

*Primary Examiner* — Jake M Vu
(74) *Attorney, Agent, or Firm* — Arrigo, Lee, Guttman & Mouta-Bellum LLP

(57) ABSTRACT

MRI contrast agent for use in the diagnosis of early changes in the endothelium of blood vessels.

5 Claims, 3 Drawing Sheets

Figure 1:
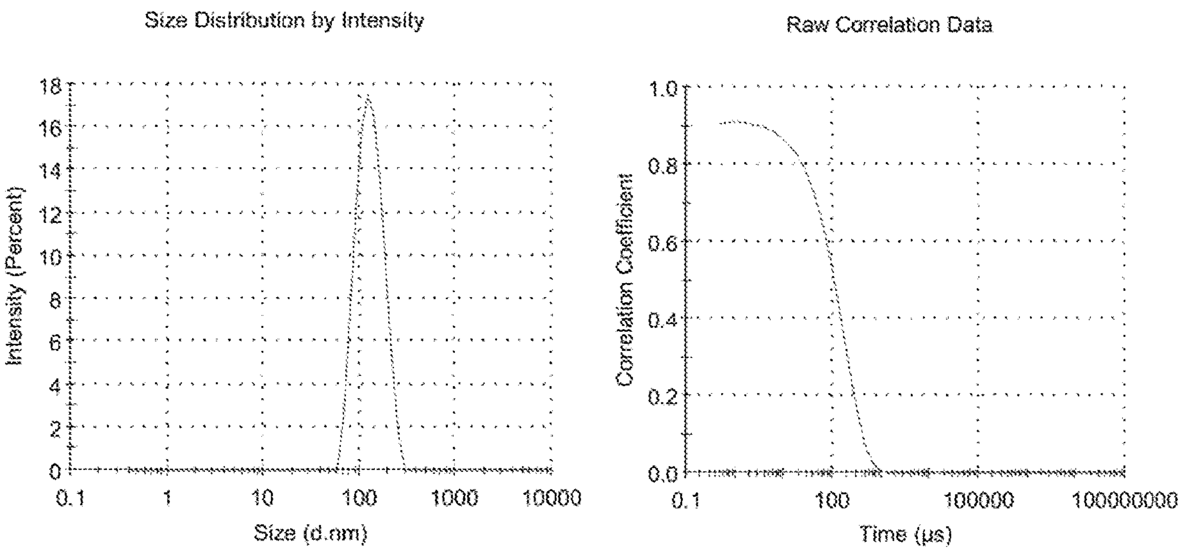

MRI CONTRAST AGENT FOR USE IN THE DIAGNOSIS OF EARLY CHANGES IN THE ENDOTHELIUM OF BLOOD VESSELS

STATE OF THE ART

The subject of the present invention is the MRI contrast agent for non-invasive diagnostics of early changes occurring in the course of the development of endothelial dysfunction of the blood vessels, which is accompanied by difficult to monitor local biochemical changes and small changes in the ultrastructure of endothelium and blood vessel wall. This contrast agent has the form of a hydrophilic complex containing Gd-diethylenetriaminepentaacetate-bis (methylamide). Gadolinium (i.e. Gd-diethylenetriaminepentaacetate-bis(methylamide)) is commonly used as a magnetic resonance imaging (MRI) contrast agent in cardiovascular diagnostics and supports procedures through intraoperative imaging, e.g. during ultrasound thermoablation$_{(1;\ 2;\ 3)}$. Gadolinium-based contrast agents available on the market are complexes, which aim to reduce their toxicity and improve their pharmacokinetics$_{(4)}$. These preparations fulfill their role in imaging of the circulatory system, however, their low molecular weight causes that they penetrate into the tissue spaces relatively quickly and nonspecifically, which significantly limits the possibilities of their use as a selective diagnostic tool in cardiovascular pathologies or in imaging of early stages of cancer. In order to use MRI imaging in the diagnosis of pathological conditions related to cardiovascular dysfunction, preparations based on nanoparticles, polymers, micelles or lipid aggregates are being developed, most often in the form of liposomes$_{(5)}$. The issue of toxicity remains unsolved in the case of nanoparticles and polymeric particles, while in the case of aggregates, such as micelles and liposomes, the main difficulty is obtaining a stable preparation when it is in the circulatory system. A partial solution to these problems is achieved by using preparations that contain complexed gadolinium. Hydrophilic complexes can be used alone (Gd-diethylenetriaminepentaacetate-bis(methylamide)), while amphiphilic complexes have a high affinity for lipid aggregates$_{(6)}$. When low molecular weight hydrophilic complexes are used, low selectivity and undesirable pharmacokinetic parameters are obtained, whereas, due to the high polarity of gadolinium, the affinity of the amphiphilic complex for the lipid membrane is limited, which results in low stability of the complex.

An example of the use of liposomes as an MRI contrast agent is that presented in patent WO2018/051289 A2, where chelated gadolinium is bound to a polymer linker anchored in the membrane with a lipid molecule. This contrast agent is intended for MRI diagnostics in pregnant women.

One of the unmet medical needs is the ability to detect early the changes in vascular endothelial phenotype, enabling early pharmacological intervention to prevent disease progression. Homeostasis of blood vessels and the cardiovascular system is controlled by endothelial function, which is responsible for the regulation of many important processes, such as endothelial permeability, blood flow, thrombotic, fibrinolytic and inflammatory processes$_{(10)}$. In the case of endothelial dysfunction, homeostasis is disturbed, which is a sign of many cardiovascular diseases and has diagnostic and therapeutic significance in atherosclerosis, hypertension, heart failure and in many other diseases such as e.g. cancers$_{(11)}$. One of the basic features of endothelial dysfunction is a disorder of the local and NO-dependent control of the lumen of blood vessels, and the degree of this impairment can be the indicator of the progression of endothelial dysfunction and cardiovascular diseases$_{(12)}$. The assessment of NO-dependent change in the lumen of blood vessels is based on measuring the diameter of blood vessels in response to a chemical or physical agent using a variety of measurement methods including angiography, plethysmography, tonometry or Doppler ultrasonography$_{(13)}$. In clinical conditions, invasive methods have limited use. Non-invasive methods are a desirable alternative and are currently widely used to assess endothelium-dependent function of blood vessel wall, including assessment of flow-mediated dilation (FMD) in the brachial artery$_{(14)}$ measured by ultrasound or reactive hyperemia (RH-PAT) in peripheral blood circulation$_{(15)}$.

Magnetic resonance imaging (MRI) can also provide information on the condition of the wall of blood vessels with high spatio-temporal resolution in a way that allows the assessment of the functional status the endothelium$_{(16)}$. In vivo MRI is also the preferred technique for assessing endothelium in experimental animals$_{(17)}$. The simultaneous measurement of endothelium-dependent vascular diameter and endothelial permeability using MRI provides unique opportunities for non-invasive insight into endothelial function in vivo$_{(18)}$.

The subject of the invention is a contrast agent for use in the diagnosis of early changes in the vascular endothelial function indicative of endothelial dysfunction, and it is in the form of an aqueous suspension containing Gd-diethylenetriaminepentaacetate-bis(methylamide), as a hydrophilic contrast agent, encapsulated within single-layer liposomes of a size from 50 nm to 200 nm, wherein the lipid membrane of liposomes is composed of a mixture containing: phosphatidylcholine, cholesterol and polyethylene glycol covalently linked to the phosphatidylethanolamine molecule (PEG-PE).

Preferably, the molar ratio of contrast agent to lipid components is from 1:1000 to 5:1, most preferably from 1:50 to 2:1.

Preferably, the molar ratio of lipids to cholesterol in the lipid membrane is from 10:1 to 5:1.

Preferably, monolayer liposomes contain PEG2000-PE in an amount of up to 10 mol % of all amphiphilic components.

Preferably, the MRI contrast agent according to the invention contains at least one of the components selected from the group comprising: caldiamide, sodium hydroxide, osmotically active substance, antioxidant, and/or a mixture thereof.

Preferably, the contrast according to the invention contains, as the osmotically active substance, a substance selected from the group comprising saline, mono- or disaccharide solution and/or a mixture thereof.

Preferably, the concentration of the hydrophilic contrast agent in the aqueous phase of the suspension is from 1 to 200 g/L.

The present invention is liposomes containing a hydrophilic MRI contrast agent for assessing endothelial function based on changes in endothelial permeability. The combination of efficiently encapsulated contrast agent with a well-characterized liposome carrier with well-defined sizes and biochemical composition allows the determination of changes in endothelium of blood vessels with sensitivity sufficient to diagnose endothelial function in experimental animals and humans.

The essence of the solution according to the invention is a new MRI contrast agent dedicated to the early diagnosis and later monitoring of the dysfunction of vascular endothelium. The new MRI contrast agent consists of Gd-diethylenetriaminepentaacetate-bis(methylamide) encapsulated within single-layer liposomes. The composition and size of these liposomes are adapted to the pathophysiology of endothelial dysfunction. The building blocks of the liposome wall are biologically neutral phospholipids and cholesterol, which makes the liposome wall impermeable, and polyethylene glycol covalently bound to the phospholipid, which ensures long-lasting circulation of liposomes in the bloodstream, and, as a consequence, their accumulation in the blood vessel wall with a pathologically changed vascular endothelium. The sizes of liposomes are selected in such a way that they can penetrate the vessel wall with a pathologically changed vascular endothelium. The diameter of the monolayer liposomes according to the invention is in the range from 50 to 200 nm.

The unilamellar liposomes may contain an amphiphilic component selected from the group comprising phospholipids, sphingolipids, chemically modified lipids and sterols, especially phosphatidylcholines and/or mixtures thereof, preferably mixtures of phosphatidylcholine with polyethylene glycol covalently bonded to a phosphatidylethanolamine molecule (PEG-PE) or a mixture of phosphatidylcholine with cholesterol and PEG-PE.

The use of hydrophilic contrast (Gd-diethylenetriaminepentaacetate-bis(methylamide)) encapsulated in the aqueous interior of liposomes solves most of the difficulties described above. The disclosed invention, combined with the possibility of modifying liposome parameters (size, surface charge or surface accessibility) allows obtaining MRI contrast agents with parameters enabling diagnosis of early endothelial dysfunction, and not only late stages of disease caused by endothelial dysfunction, as is the case with the detection of atherosclerotic changes, or advanced vasculitis (7; 8; 9).

The described solution differs from the known solutions, which are based on the affinity of the liposome-bounded ligand or antibody specific to the receptor or epitope in order to ensure cellular or tissue specificity. The solution according to the invention has tissue selectivity utilizing the correlation between tissue (endothelium) topology and integrity, and liposome parameters. According to the invention, it has been surprisingly found that diagnostics of endothelial dysfunction requires that the diameter of liposomes not exceed 200 nm so that they can easily penetrate under the vascular endothelium layer.

The solution according to the invention is illustrated by the following examples and Figures, which do not limit the scope of its protection in any way.

Liposomes were prepared according to the procedure disclosed in patent PCT/EP2018/057400 "High-efficiency encapsulation of hydrophilic compounds in unilamellar liposomes" where gadolinium in the aqueous phase is combined with a high concentration of lipid dissolved in propylene glycol. Amphiphilic substances that are the building blocks of liposomes should have a log P value greater than 5 to ensure their stability in physiological fluids. As a result, liposomes with a high gadolinium content are obtained differently than in the method disclosed in the patent US 2012/0141381 A1 "Methods for loading contrast agents into a liposome" where lipids are hydrated after being mixed in an organic solvent, which is removed before liposomes are formed.

EXAMPLE 1

Gd-diethylenetriaminepentaacetate-bis(methylamide), also known as gadodiamide, dissolved in an aqueous solution of sodium caldiamide at pH 7.45 was added to purified phosphatidylcholine (Lipoid GmbH, Germany) dissolved in propylene glycol. The whole mixture was stirred at 60° C. until a homogeneous, milky suspension was formed. Then the suspension thus obtained was extruded through polycarbonate filters with a pore diameter of 100 nm to obtain a homogenous liposome gel characterized by uniform size of liposomes encapsulating the contrast agent.

TABLE 1

Contrast agent composition.

| | % by weight |
|---|---|
| CONTRAST AGENT: | |
| Gd-diethylenetriaminepentaacetate-bis(methylamide) | 14.8 |
| ADDITIONAL SUBSTANCES: | |
| Purified phosphatidylcholine | 30 |
| Propylene glycol | 20 |
| Caldiamide sodium | 0.62 |
| Sodium hydroxide | 0.01 |
| Purified water | 34.57 |
| TOTAL | 100 |

The molar ratio of Gd-diethylenetriaminepentaacetate-bis (methylamide) to amphiphilic substances is about 1:2. The average size of liposomes with an encapsulated contrast agent in an aqueous solution at pH 7.4 is 124 nm with PDI=0.12. The encapsulation efficiency was 77%±5%. The encapsulation efficiency of Gd-diethylenetriaminepentaacetate-bis(methylamide) was determined by ultrafiltration.

FIG. 1 shows the homogeneity of the liposome suspension. The left panel shows the distribution of liposome sizes with an encapsulated contrast agent in a pH 7.4 aqueous solution and the right panel shows the quality of matching the correlation function to experimental data. The encapsulation efficiency was 77%±5%. The encapsulation efficiency of Gd-diethylenetriaminepentaacetate-bis(methylamide) was determined by ultrafiltration.

EXAMPLE 2

Gd-diethylenetriaminepentaacetate-bis(methylamide) dissolved in an aqueous solution of sodium caldiamide at pH 7.45 was added to purified phosphatidylcholine (Lipoid) with the addition of cholesterol dissolved in propylene glycol. The whole mixture was stirred at 60° C. until a homogeneous, milky suspension was formed. Then the suspension thus obtained was extruded through polycarbonate filters with a pore diameter of 100 nm to obtain a homogenous liposome gel characterized by uniform size of liposomes encapsulating the contrast agent.

TABLE 2

Contrast agent composition.

| | % by weight |
|---|---|
| CONTRAST AGENT: | |
| Gd-diethylenetriaminepentaacetate-bis(methylamide) | 14.8 |
| ADDITIONAL SUBSTANCES: | |
| Purified phosphatidylcholine | 27 |
| Cholesterol | 3 |
| Propylene glycol | 20 |

TABLE 2-continued

| Contrast agent composition. | |
|---|---|
| | % by weight |
| Caldiamide sodium | 0.62 |
| Sodium hydroxide | 0.01 |
| Purified water | 34.57 |
| TOTAL | 100 |

The molar ratio of Gd-diethylenetriaminepentaacetate-bis (methylamide) to amphiphilic substances is about 1:2. The average size of liposomes with an encapsulated contrast agent in an aqueous solution at pH 7.4 is 132 nm with PDI=0.17. The encapsulation efficiency was 87%±6%. The encapsulation efficiency of Gd-diethylenetriaminepentaacetate-bis(methyl amide) was determined by ultrafiltration.

Figure 2:
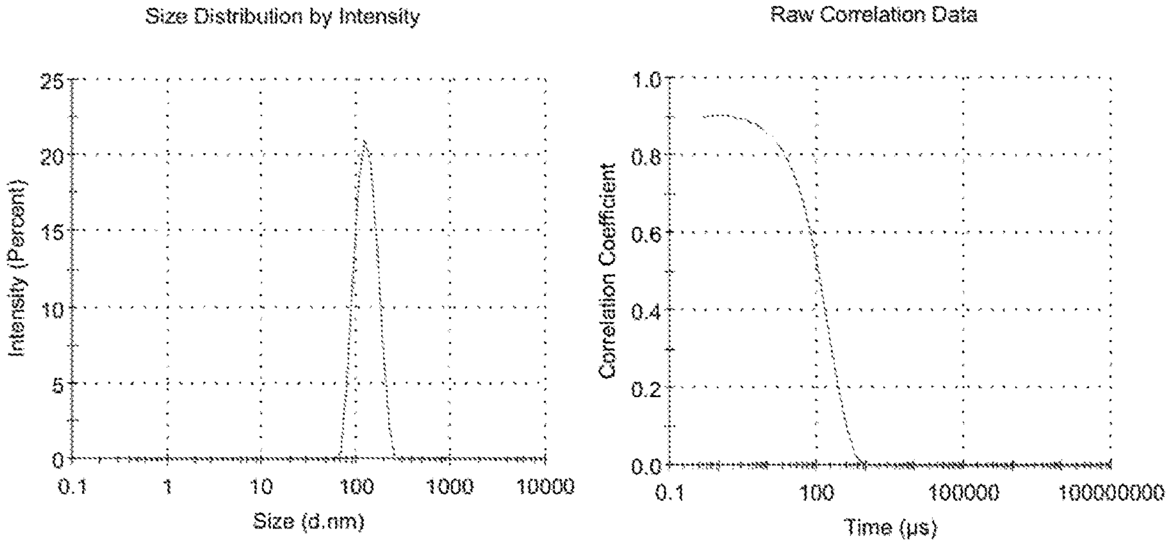

FIG. 2 shows the homogeneity of the liposome suspension. The left panel shows the distribution of liposome sizes with an encapsulated contrast agent in a pH 7.4 aqueous solution and the right panel shows the quality of matching the correlation function to experimental data. The encapsulation efficiency was 87%±6%. The encapsulation efficiency of gadolinium was determined using ultrafiltration. Example 2 shows that the lipid composition of the liposome can change the encapsulation efficiency of Gd-diethylenetriaminepentaacetate-bis(methyl amide).

EXAMPLE 3

Gd-diethylenetriaminepentaacetate-bis(methylamide) dissolved in an aqueous solution of sodium caldiamide at pH 7.45 was added to purified phosphatidylcholine (Lipoid) with the addition of cholesterol and PEG-PE (polyethylene glycol with a molecular weight of 2000 Da covalently bound to a phosphatidylethanolamine molecule) dissolved in propylene glycol. The whole mixture was stirred at 60° C. until a homogeneous, milky suspension was formed. Then the suspension thus obtained was extruded through polycarbonate filters with a pore diameter of 100 nm to obtain a homogenous liposome gel characterized by uniform size of liposomes encapsulating the contrast agent.

TABLE 3

| Contrast agent composition. | |
|---|---|
| | % by weight |
| CONTRAST AGENT: | |
| Gd-diethylenetriaminepentaacetate-bis(methylamide) | 14.8 |
| ADDITIONAL SUBSTANCES: | |
| Purified phosphatidylcholine | 22 |
| Cholesterol | 6 |
| PEG-PE | 2 |
| Propylene glycol | 20 |
| Caldiamide sodium | 0.62 |
| Sodium hydroxide | 0.01 |
| Purified water | 34.57 |
| TOTAL | 100 |

The molar ratio of Gd-diethylenetriaminepentaacetate-bis (methylamide) to amphiphilic substances is about 1:2. The average size of liposomes with an encapsulated contrast agent in an aqueous solution at pH 7.4 is 120 nm with PDI=0.2. The encapsulation efficiency was 74%±8%. The encapsulation efficiency of Gd-diethylenetriaminepentaacetate-bis(methylamide) was determined by ultrafiltration.

EXAMPLE 4

Gd-diethylenetriaminepentaacetate-bis(methylamide) dissolved in an aqueous solution of sodium caldiamide at pH 7.45 was added to purified phosphatidylcholine (Lipoid) dissolved in propylene glycol. The whole mixture was stirred at 60° C. until a homogeneous, milky suspension was formed. Then the suspension thus obtained was extruded through polycarbonate filters with a pore diameter of 100 nm to obtain a homogenous liposome gel characterized by uniform size of liposomes encapsulating the contrast agent.

TABLE 4

| Contrast agent composition. | |
|---|---|
| | % by weight |
| CONTRAST AGENT: | |
| Gd-diethylenetriaminepentaacetate-bis(methylamide) | 20 |
| ADDITIONAL SUBSTANCES: | |
| Purified phosphatidylcholine | 30 |
| Propylene glycol | 20 |
| Caldiamide sodium | 0.84 |
| Sodium hydroxide | 0.01 |
| Purified water | 29.15 |
| TOTAL | 100 |

The molar ratio of Gd-diethylenetriaminepentaacetate-bis (methylamide) to amphiphilic substances is about 2:3. The average size of liposomes with an encapsulated contrast agent in an aqueous solution at pH 7.4 is 105 nm with PDI=0.15. The encapsulation efficiency was 82%±5%. The encapsulation efficiency of Gd-diethylenetriaminepentaacetate-bis(methyl amide) was determined by ultrafiltration.

EXAMPLE 5

Gd-diethylenetriaminepentaacetate-bis(methylamide) dissolved in an aqueous solution of sodium caldiamide at pH 7.45 was added to purified phosphatidylcholine (Lipoid) dissolved in propylene glycol. The whole mixture was stirred at 60° C. until a homogeneous, milky suspension was formed. Then the suspension thus obtained was extruded through polycarbonate filters with a pore diameter of 100 nm to obtain a homogenous liposome gel characterized by uniform size of liposomes encapsulating the contrast agent.

TABLE 5

| Contrast agent composition. | |
|---|---|
| | % by weight |
| CONTRAST AGENT: | |
| Gd-diethylenetriaminepentaacetate-bis(methylamide) | 0.1 |
| ADDITIONAL SUBSTANCES: | |
| Purified phosphatidylcholine | 30 |
| Propylene glycol | 20 |
| Caldiamide sodium | 0.01 |

TABLE 5-continued

| Contrast agent composition. | |
|---|---|
| | % by weight |
| Sodium hydroxide | 0.01 |
| Purified water | 49.88 |
| TOTAL | 100 |

The molar ratio of Gd-diethylenetriaminepentaacetate-bis (methylamide) to amphiphilic substances is about 1:300. The average size of liposomes with an encapsulated contrast agent in an aqueous solution at pH 7.35 is 110 nm with PDI=0.1. The encapsulation efficiency was 84%±6%. The encapsulation efficiency of Gd-diethylenetriaminepentaacetate-bis(methyl amide) was determined by ultrafiltration.

EXAMPLE 6

Gd-diethylenetriaminepentaacetate-bis(methylamide) dissolved in an aqueous solution of sodium caldiamide at pH 7.45 was added to purified phosphatidylcholine (Lipoid) dissolved in glycerol. The whole mixture was stirred at 60° C. until a homogeneous, milky suspension was formed. Then the suspension thus obtained was extruded through polycarbonate filters with a pore diameter of 100 nm to obtain a homogenous liposome gel characterized by uniform size of liposomes encapsulating the contrast agent.

TABLE 6

| Contrast agent composition. | |
|---|---|
| | % by weight |
| CONTRAST AGENT: | |
| Gd-diethylenetriaminepentaacetate-bis(methylamide) | 1 |
| ADDITIONAL SUBSTANCES: | |
| Purified phosphatidylcholine | 30 |
| Glycerol | 20 |
| Caldiamide sodium | 0.04 |
| Sodium hydroxide | 0.01 |
| Purified water | 48.95 |
| TOTAL | 100 |

The molar ratio of Gd-diethylenetriaminepentaacetate-bis (methylamide) to amphiphilic substances is about 1:30. The average size of liposomes with an encapsulated contrast agent in an aqueous solution at pH 7.4 is 106 nm with PDI=0.12. The encapsulation efficiency was 86%±7%. The encapsulation efficiency of Gd-diethylenetriaminepentaacetate-bis(methyl amide) was determined by ultrafiltration.

EXAMPLE 7

Gd-diethylenetriaminepentaacetate-bis(methylamide) dissolved in saline at pH 7.45 was added to purified phosphatidylcholine (Lipoid) and vitamin E dissolved in propylene glycol. The whole mixture was stirred at 60° C. until a homogeneous, milky suspension was formed. Then the suspension thus obtained was extruded through polycarbonate filters with a pore diameter of 100 nm to obtain a homogenous liposome gel characterized by uniform size of liposomes encapsulating the contrast agent.

TABLE 7

| Contrast agent composition. | |
|---|---|
| | % by weight |
| CONTRAST AGENT: | |
| Gd-diethylenetriaminepentaacetate-bis(methylamide) | 1 |
| ADDITIONAL SUBSTANCES: | |
| Purified phosphatidylcholine | 20 |
| Propylene glycol | 30 |
| Sodium hydroxide | 0.01 |
| Vitamin E | 1 |
| Saline | 47.99 |
| TOTAL | 100 |

The molar ratio of Gd-diethylenetriaminepentaacetate-bis (methylamide) to amphiphilic substances is about 1:20. The average size of liposomes with an encapsulated contrast agent in an aqueous solution at pH 7.4 is 112 nm with PDI=0.21. The encapsulation efficiency was 88%±6%. The encapsulation efficiency of Gd-diethylenetriaminepentaacetate-bis(methyl amide) was determined by ultrafiltration.

EXAMPLE 8

Gd-diethylenetriaminepentaacetate-bis(methylamide) dissolved in an aqueous solution of sodium caldiamide at pH 7.45 was added to purified phosphatidylcholine (Lipoid) dissolved in propylene glycol. The whole mixture was stirred at 60° C. until a homogeneous, milky suspension was formed. Then the suspension thus obtained was extruded through polycarbonate filters with a pore diameter of 100 nm to obtain a homogenous liposome gel characterized by uniform size of liposomes encapsulating the contrast agent.

TABLE 8

| Contrast agent composition. | |
|---|---|
| | % by weight |
| CONTRAST AGENT: | |
| Gd-diethylenetriaminepentaacetate-bis(methylamide) | 14.8 |
| ADDITIONAL SUBSTANCES: | |
| Purified phosphatidylcholine | 20 |
| Propylene glycol | 20 |
| Caldiamide sodium | 0.62 |
| Sodium hydroxide | 0.01 |
| Purified water | 44.57 |
| TOTAL | 100 |

The molar ratio of Gd-diethylenetriaminepentaacetate-bis (methylamide) to amphiphilic substances is about 1:20. The average size of liposomes with an encapsulated contrast agent in an aqueous solution at pH 7.4 is 118 nm with PDI=0.1. The encapsulation efficiency was 82%±6%. The encapsulation efficiency of Gd-diethylenetriaminepentaacetate-bis(methylamide) was determined by ultrafiltration.

The Effectiveness of MRI Contrast According to the Invention was Tested in an Animal Model of Endothelial Dysfunction.

Animal Model of Endothelial Dysfunction

The experiments were performed using female ApoE/LDLR$_{-/-}$ mice of different ages: 4-, 6-, 8-, 12- and 28-week-old$_{(19)}$ in comparison to control young (8-week-old) mice (C57BL/6) without endothelial dysfunction. All mice (body weight 20-30 g) were housed under standard pathogen-free conditions (LD: 12/12, humidity: 60%, temperature: 23° C.).

Magnetic Resonance Imaging (MRI)

MRI experiments were carried out using a 9.4 T scanner (BioSpec 94/20 USR, Bruker, Germany). During the experiment, mice were anesthetized using isoflurane (Aerrane, Baxter Sp. z o.o., Poland, 1.5% by volume) in an oxygen and air mixture (1:2). Cardiac activity, respiration rate and body temperature (maintained at 37° C., using circulating warm water) were monitored using Monitoring and Gating System (SA Inc., Stony Brook, NY, USA). Mice were imaged in the supine position to test endothelial function and permeability in various blood vessels.

In Vivo MRI Protocol for the Assessment of Endothelial Permeability

Endothelial permeability measurements were performed using two gadolinium contrast agents (CA); reference gadolinium albumin binding contrast agent (Galbumin, BioPAL, Worcester, MA, USA—25 mg/mL, 4.5 mL/kg, iv) and new preparation according to the invention—Gd-diethylenetriaminepentaacetate-bis(methylamide) placed inside liposomes. Relaxation time ($T_1$) before and 30 min after intravenous CA administration was measured to assess BCA permeability using the VFA technique$_{(20)}$, by sampling the signal using varying values of flip angles (FA), and then fitting the result to the expected $T_1$-dependent signal model$_{(21)}$. 3D images of the aortic arch were acquired using the 3D IG-FLASH sequence, to obtain high Bi field profile uniformity within measured subslices. Imaging parameters included the following: $T_R$ 10 ms, $T_E$ 1.1 ms, FOV 30×30×4 $mm_3$, matrix size 192×160×8, number of repetitions 12. Eight FAs were used: 2°, 4°, 6°, 8°, 14°, 20°, 30° and 50°. FA values were set by changing the RF pulse length with constant amplifier power. The total scanning time for all angles was 16 min.

Data analysis: The obtained images were used to calculate $T_1$ maps before and after CA administration. The signal model was fitted pixel by pixel using Matlab software. Two $T_1$ maps (before and after CA administration) were compared to estimate the number of pixels for which $T_1$ had changed significantly (by more than 50%) after CA administration (Npx50, marked in red in FIG. 3C). The threshold (50%) was determined experimentally.

Figure 3:
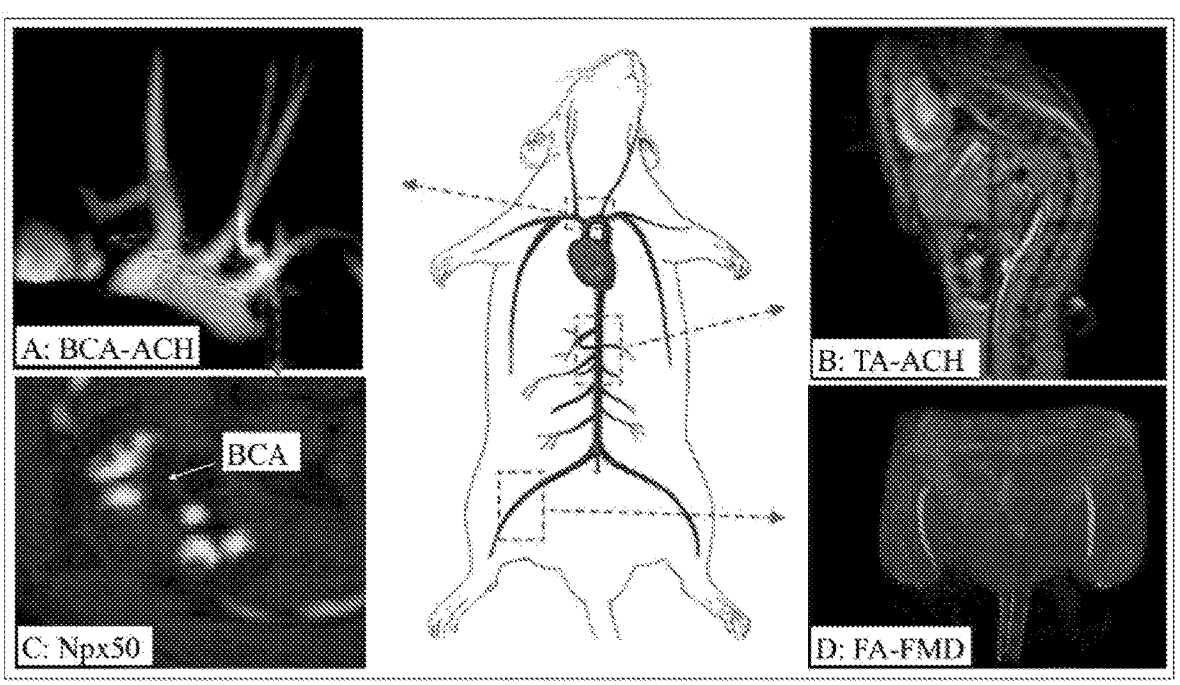

FIG. 3 shows an illustration of the methodology for MRI-based in vivo assessment of endothelium-dependent response and endothelial permeability. Endothelium-dependent response to acetylcholine (Ach), expressed as changes in vessel volume, was assessed in the brachiocephalic artery (BCA) visible on the 3D image of the aortic arch (A) and in the abdominal aorta (AA) positioned on the sagittal view of the mouse (B). Assessment of vessel response to flow-mediated dilation (FMD), also expressed as changes in vessel volume, was performed in the femoral artery (FA), visible on the 3D image of the left hind limb (D). Pixels for which $T_1$ had changed more than 50% after CA (Npx50) were marked in red on a representative cross-sectional image of blood vessels arising from the aortic arch (C).

The obtained data are presented as the mean and standard deviation. Statistical tests were done using STATISTICA 10 (Stat Soft Inc., USA) using a parametric test (one-way analysis of variance (ANOVA) with a Tukey test). A p value of 0.05 was considered statistically significant.

Demonstration that the Subject of the Invention in the Form of a Hydrophilic Gadolinium Encapsulated in Liposomes is an MRI Contrast Agent for the Detection of Early Changes in the Endothelium of Blood Vessels.

Prepared liposomes, in which Gd-diethylenetriaminepentaacetate-bis(methylamide) (GD liposome) was encapsulated were used as a magnetic resonance imaging (MRI) contrast agents for in vivo detection of endothelial dysfunction based on changes in endothelial permeability in ApoE/$LDLR_{-/-}$ mice. For comparison, assessment of the endothelial permeability was performed using albumin-binding gadolinium contrast agent (GD albumin).

The Development of Increased Endothelial Permeability in Brachiocephalic Artery (BCA) in ApoE/$LDLR_{-/-}$ Mice In the presented experiment, the contrast agent having the composition of Example 8 was used. As shown in FIG. 4B, the preparation of Gd-diethylenetriaminepentaacetate-bis (methylamide) encapsulated in the liposome allowed the detection of early changes in endothelial permeability, observed as an increase in Npx50, which was already observed in 4-week-old ApoE/$LDLR_{-/-}$ mice (Npx50: increase by 100% in comparison to control mice, C57BL/6). Changes in endothelial permeability were exacerbated by atherosclerosis progression in ApoE/$LDLR_{-/-}$ mice, and a 4-fold increase in Npx50 was observed in 28-week-old ApoE/$LDLR_{-/-}$ mice. In contrast to the administration of the liposomal contrast agent, intravenous injection of GD albumin caused significant changes in the Npx50 parameter (increase by about 100%) only in 28-week-old ApoE/$LDLR_{-/-}$ mice, Furthermore, in 4-12-week-old ApoE/$LDLR_{-/-}$ mice did not show a significant increase in vascular wall permeability assessed using GD albumin (increase in Npx50 between 3% and 30%, in comparison to control mice; FIG. 4A).

Figure 4:
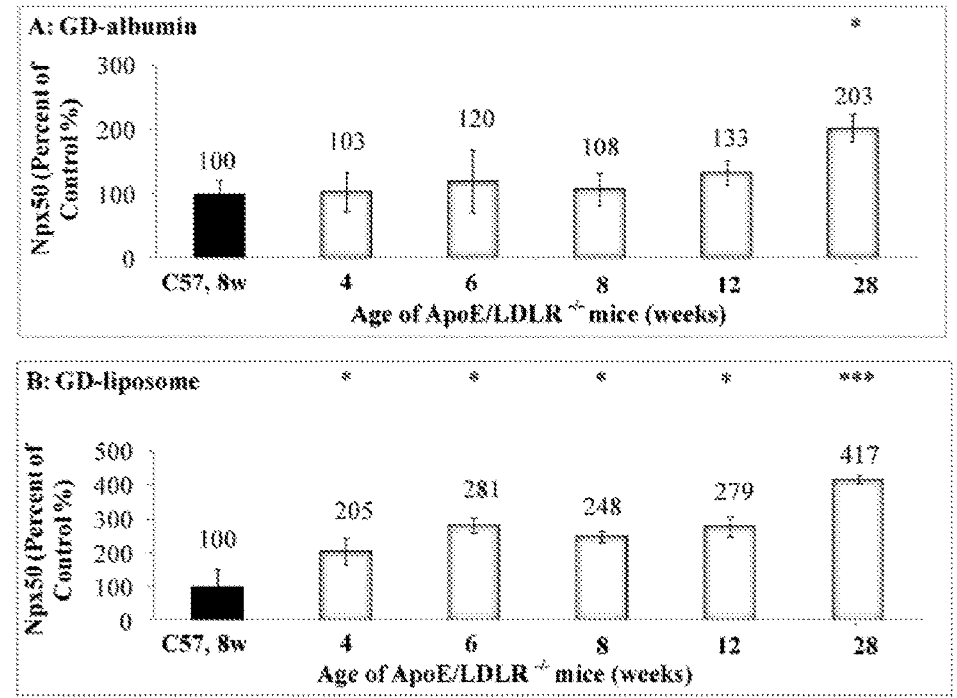

FIG. 4 shows an increase of the endothelial permeability in brachiocephalic artery in ApoE/$LDLR_{-/-}$ mice. Number of pixels around BCA lumen for which $T_1$ has changed by more than 50% (Npx50) after using albumin-binding gadolinium (A: GD-albumin) contrast agent or Gd-diethylenetriaminepentaacetate-bis(methylamide) encapsulated in liposomes (B: GD-liposome) are expressed as a percentage of control in ApoE/$LDLR_{-/-}$ mice (white columns) of different ages: 4-week-old ApoE/$LDLR_{-/-}$ mice (ApoE_4 W, n=4), 6-week-old ApoE/$LDLR_{-/-}$ mice (ApoE_6 W, n=4), 8-week-old ApoE/$LDLR_{-/-}$ mice (ApoE_8 W, n=6), 12-week-old ApoE/$LDLR_{-/-}$ mice (ApoE_12 W, n=5) and 28-week-old ApoE/$LDLR_{-/-}$ mice ((ApoE_28 W, n=6). Control is 8-week-old C57BL/6 mice (C57_8W, n=6, black columns).

Figure 5:
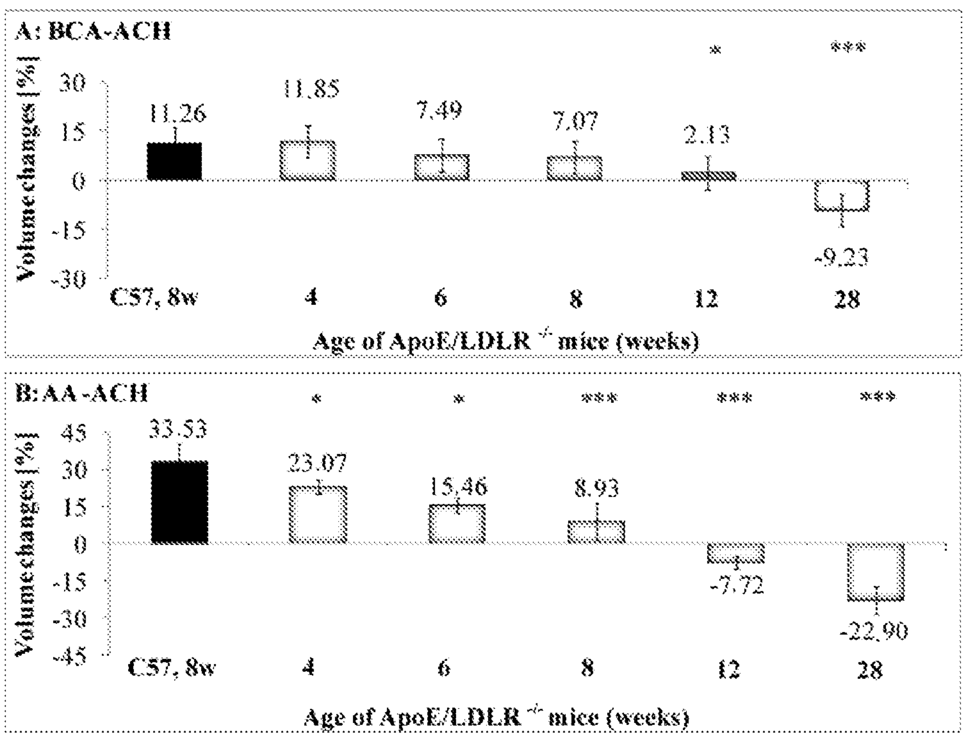
Figure 6:
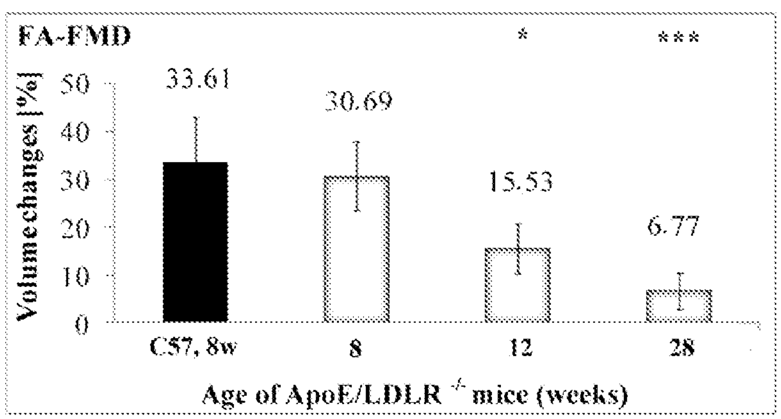

Progression of an Impairment of the Endothelium-Dependent Response to Acetylcholine Administration in the BCA and the Abdominal Aorta (AA) in ApoE/$LDLR_{-/-}$ Mice To assess the sensitivity of endothelial dysfunction detection using the new contrast agent, being an invention, impaired endothelial function in ApoE/LDLR−/− mice was also assessed by other MRI-based techniques; detection of endothelium-dependent response to acetylcholine (FIG. 5) and measurement of increase in flow after short-term vessel occlusion (FMD, FIG. 6). As described in our recent publication$_{(22)}$, endothelium-dependent response to acetylcholine (Ach, FIG. 5B) in abdominal aorta (AA) is the most sensitive in vivo method to detect changes in endothelial phenotype. Intraperitoneal administration of Ach resulted in the detection of significantly impaired AA functional response in 4-week-old ApoE/$LDLR_{-/-}$ mice (AA volume change: about 23% in comparison to about 34% in control mice). Further progression of the impairment of the AA response to Ach was observed in 6-8-week-old ApoE/LDLR$_{-/-}$ mice and as the paradoxical vasoconstriction in 12- and 28-week-old ApoE/LDLR$_{-/-}$ mice (change in AA volume: about −8% and −23%, respectively). Changes in the BCA endothelial function, described as impaired endothelium-dependent vasodilatation in response to Ach, were only observed in 12-week-old mice (volume changes: about 2%, FIG. 5A). The BCA response to Ach in 4 to 8-week-old ApoE/LDLR$_{-/-}$ mice remained unchanged (changes in BCA volume: approximately 10%) and was comparable to the normal vasodilatatory response observed in the 8-week-old control mice (volume change in the BCA: 11.26%). Moreover, impairment of endothelium-dependent response to increase in flow after short-term vessel occlusion (FMD) was observed not earlier than in 12-week-old ApoE/LDLR$_{-/-}$ mice (volume change in the FA: about 16% in comparison to about 34% in control mice, FIG. 6). FMD response in younger, 8-week-old ApoE/LDLR$_{-/-}$ mice remained unchanged, as compared to control mice (FA volume change: about 31%).

These experiments clearly show that the assessment of changes in endothelial permeability using the liposomal contrast agent being an invention, allows the detection of functional changes in vascular endothelium at a similar early stage of endothelial dysfunction development as the assessment of endothelial-dependent response to Ach administration in in abdominal aorta, which was the most sensitive method for detection of changes in endothelial phenotype, in our previous studies[22]. The detection of functional changes in BCA as well as in the FMD response, the latter is the gold standard in the assessment of endothelial function in clinical conditions[12,13], was possible at a later stage of endothelial dysfunction development, in comparison to the assessment using a liposomal contrast agent being a subject of an invention.

FIG. 5 shows the progression of the impaired endothelium-dependent response to acetylcholine administration in the brachiocephalic artery and the abdominal aorta in ApoE/LDLR$_{-/-}$ mice. Changes in the end-diastolic volume of brachiocephalic artery (A: BCA-ACH) and abdominal aorta (B: AA-ACH) 25 minutes after administration of acetylcholine in ApoE/LDLR$_{-/-}$ mice (white columns) of different ages: 4-week-old ApoE/LDLR$_{-/-}$ mice, 6-week-old ApoE/LDLR$_{-/-}$ mice, 8-week-old ApoE/LDLR$_{-/-}$ mice, 12-week-old ApoE/LDLR$_{-/-}$ mice, 28-week-old ApoE/LDLR$_{-/-}$ mice as compared to 8-week-old control C57BL/6 mice, (C57_8W, n=4, black columns). Statistics: one-way ANOVA followed by Tukey's post hoc test (normality was assessed using the Shapiro-Wilk test); *p<0.05, p<0.01, *p<0.001.

FIG. 6 shows the progression of the impaired endothelium-dependent response to an increase in flow after short term vessel occlusion (FMD) in the femoral artery (FA) in ApoE/LDLR$_{-/-}$ mice of different ages: 8-week-old ApoE/LDLR$_{-/-}$ mice (ApoE_8 W, n=6), 23-week-old ApoE/LDLR$_{-/-}$ mice (ApoE_12 W, n=6) and 28-week-old ApoE/LDLR$_{-/-}$ mice (ApoE_28 W, n=5), as compared to the 8-week-old control C57BL/6 mice (C57_8W, n=5, black columns). Statistics: one-way ANOVA followed by Tukey's post hoc test (normality was assessed using the Shapiro-Wilk test); *p<0.05, p<0.01, *p<0.001.

REFERENCES

1. Kim H K, Lee G H, Chang Y (2018) Gadolinium as an MRI contrast agent. *Future Med Chem* 10, 639-661.
2. Ibrahim M A, Dublin A B (2018) Magnetic Resonance Imaging (MRI), Gadolinium. In *StatPearls*. Treasure Island (FL).
3. de Smet M, Heilman E, Langereis S et al. (2011) Magnetic resonance imaging of high intensity focused ultrasound mediated drug delivery from temperature-sensitive liposomes: An in vivo proof-of-concept study. *J Control Release* 150, 102-110.
4. Le Fur M, Caravan P (2018) The biological fate of gadolinium-based MRI contrast agents: a call to action for bioinorganic chemists. Metallomics.
5. Lux J, Sherry A D (2018) Advances in gadolinium-based MRI contrast agent designs for monitoring biological processes in vivo. *Curr Opin Chem Biol* 45, 121-130.
6. Glogard C, Stensrud G, Hovland R et al. (2002) Liposomes as carriers of amphiphilic gadolinium chelates: the effect of membrane composition on incorporation efficacy and in vitro relaxivity. *Int J Pharmaceut* 233, 131-140.
7. Erdogan S, Medarova Z O, Roby A et al. (2008) Enhanced tumor MR imaging with gadolinium-loaded polychelating polymer-containing tumor-targeted liposomes. *J Magn Reson Imaging* 27, 574-580.
8. Jin Y Q, Zhang N P, Li C L et al. (2017) Nanosystem composed with MSNs, gadolinium, liposome and cytotoxic peptides for tumor theranostics. Colloid Surface B 151, 240-248.
9. Nitta N, Takakusagi Y, Kokuryo D et al. (2018) Intratumoral evaluation of 3D microvasculature and nanoparticle distribution using a gadolinium-dendron modified nano-liposomal contrast agent with magnetic resonance micro-imaging. *Nanomed-Nanotechnol* 14, 1315-1324.
10. Franses J W, Drosu N C, Gibson W J et al. (2013) Dysfunctional endothelial cells directly stimulate cancer inflammation and metastasis. *Int J Cancer* 133, 1334-1344.
11. Walczak M, Suraj J, Kus K et al. (2015) Towards a comprehensive endothelial biomarkers profiling and endothelium-guided pharmacotherapy. *Pharmacol Rep* 67, 771-777.
12. Frolow M, Drozdz A, Kowalewska A et al. (2015) Comprehensive assessment of vascular health in patients; towards endothelium-guided therapy. *Pharmacol Rep* 67, 786-792.
13. Raitakari O T, Celermajer D S (2000) Flow-mediated dilatation. *Br J Clin Pharmacol* 50, 397-404.
14. Phinikaridou A, Hua N, Pham T et al. (2013) Regions of low endothelial shear stress colocalize with positive vascular remodeling and atherosclerotic plaque disruption: an in vivo magnetic resonance imaging study. *Circ Cardiovasc Imaging* 6, 302-310.
15. van Bochove G S, Straathof R, Krams R et al. (2010) MRI-determined carotid artery flow velocities and wall shear stress in a mouse model of vulnerable and stable atherosclerotic plaque. *MAGMA* 23, 77-84.
16. Davignon J, Ganz P (2004) Role of endothelial dysfunction in atherosclerosis. *Circulation* 109, 11127-32.
17. Bar A, Skorka T, Jasinski K et al. (2016) Retrospectively gated MRI for in vivo assessment of endothelium-dependent vasodilatation and endothelial permeability in murine models of endothelial dysfunction. *Nmr Biomed* 29, 1088-1097.
18. Morawski A M, Winter P M, Crowder K C et al. (2004) Targeted nanoparticles for quantitative imaging of sparse molecular epitopes with MRI. *Magn Reson Med* 51, 480-486.
19. Ishibashi S, Herz J, Maeda N et al. (1994) The two-receptor model of lipoprotein clearance: tests of the hypothesis in "knockout" mice lacking the low density lipoprotein receptor, apolipoprotein E, or both proteins. *Proc Natl Acad Sci USA* 91, 4431-4435.

20. Wang J, Qiu M, Kim H et al. (2006) T1 measurements incorporating flip angle calibration and correction in vivo. *J Magn Reson* 182, 283-292.

21. Bar A, Skorka T, Jasinski K et al. (2015) MRI-based assessment of endothelial function in mice in vivo. *Pharmacol* Rep 67, 765-770.

22. Bar A, Targosz-Korecka M, Suraj J et al. (2019) Degradation of Glycocalyx and Multiple Manifestations of Endothelial Dysfunction Coincide in the Early Phase of Endothelial Dysfunction Before Atherosclerotic Plaque Development in Apolipoprotein E/Low-Density Lipoprotein Receptor-Deficient Mice. *J Am Heart Assoc.* 2019 Mar. 19; 8(6):e011171

The invention claimed is:

1. An MRI contrast agent for use in the diagnosis of early changes in blood vessel endothelium, in the form of an aqueous suspension containing as a hydrophilic contrast agent Gd-diethylenetriaminepentaacetate-bis (methylamide) encapsulated within single-layer liposomes from 50 nm to 200 nm in size, wherein the lipid membrane of the liposomes is made of a mixture containing: purified phosphatidylcholine that has not been hydrogenated, cholesterol and polyethylene glycol covalently bounded to a phosphatidylethanolamine molecule (PEG-PE) to lengthen circulation of liposomes in the bloodstream.

2. The contrast agent according to claim 1, characterized in that the molar ratio of contrast agent to lipid components is from 1:50 to 2:1.

3. The contrast agent according to claim 1, characterized in that it further contains caldiamide.

4. The contrast agent according to claim 3, characterized in that it further contains an osmotically active substance selected from the group consisting of saline, mono- or disaccharide solution and mixtures thereof.

5. The contrast agent according to claim 1, characterized in that the concentration of the hydrophilic contrast agent in the aqueous phase of the suspension is from 1 to 200 g/L.

* * * * *